United States Patent [19]

Clarke

[11] Patent Number: 4,626,215
[45] Date of Patent: Dec. 2, 1986

[54] MASTICATION-ENHANCING PROTRUSION

[76] Inventor: Clifford R. Clarke, 1600 Atkins, Apt. 12, Eugene, Oreg. 97401

[21] Appl. No.: 764,388

[22] Filed: Aug. 12, 1985

[51] Int. Cl.⁴ .............................................. A61C 13/08
[52] U.S. Cl. .................................... 433/198; 433/206
[58] Field of Search ........................ 433/205, 206, 198

[56] References Cited

U.S. PATENT DOCUMENTS 1,377,358  5/1921  Lowry ................................. 433/206
2,598,769  6/1952  Donavan .
3,277,575  10/1966  Stasiw ................................. 433/198

Primary Examiner—Robert Peshock
Attorney, Agent, or Firm—Kolisch, Hartwell & Dickinson

[57] ABSTRACT

The mastication enhancing device of the instant invention includes a hardened cusp for providing a hardened occlusal surface in a tooth, and means for retaining the hardened cusp in a predetermined pattern in a tooth. A major portion of a hardened cusp is embedded in the tooth. Cusps may be arranged in an opposing, offset pattern in upper and lower teeth to provide a point-contact between occlusal surfaces of upper and lower teeth.

2 Claims, 4 Drawing Figures

MASTICATION-ENHANCING PROTRUSION

BACKGROUND AND SUMMARY OF THE INVENTION

The instant invention relates to dentures. Specifically, the instant invention is a protrusion for a denture or artificial tooth which enhances the ability of the prosthesis to masticate properly food.

Dentures provide the wearer with the ability to chew, or masticate, their food properly while at the same time enhancing the overall appearance of the wearer. Dentures, however, do not provide the wearer with the same chewing force as do natural teeth. This is due in large part because dentures are not fixed to the jawbones as are natural teeth. Additionally, although dentures may be properly fitted, they may cause some discomfort to the wearer and discourage the wearer from applying the maximum amount of chewing force, because of pain which may be felt when such force is applied to the gums on which the dentures are mounted.

Known devices for enhancing mastication force are somewhat effective but are not aesthetically pleasing. Additionally, known devices do not provide a maximum mastication-enhancing force because they do not provide for a point contact between the mastication-enhancing surfaces on upper and lower teeth.

An object of the instant invention is to provide a mastication-enhancing device which will provide a point contact between occlusal surfaces of the teeth.

Another object of the instant invention is to provide a mastication-enhancing device which, with lateral shifting of the teeth, provides a grinding action.

A further object of the instant invention is to provide a mastication-enhancing device which is usable with full or partial dentures, or which may be used with a crown.

Another object of the instant invention is to provide a mastication-enhancing device which is inexpensive to manufacture, easy to incorporate into denture, and which simulates the appearance of naturally occurring cusps.

The mastication enhancing devices of the instant invention includes a hardened cusp for providing a hardened occlusal surface in a tooth, and means for retaining the hardened cusp in a predetermined pattern in a tooth. A major portion of a hardened cusp is embedded in the tooth. Cusps may be arranged in an opposing, offset pattern in upper and lower teeth to provide a point-contact between occlusal surfaces of upper and lower teeth.

These and other objects and advantages of the instant invention will become more fully apparent as the description which follows is read in conjunction with the drawings.

DETAILED DESCRIPTION OF A PREFERRED EMBODIMENT

Figure 1:
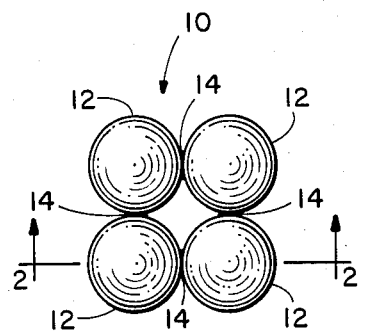
FIG. 1 shows an array of hardened cusp elements constructed according to the invention.

Turning now to the drawings, and initially to FIG. 1, a device including multiple mastication-enhancing protrusions is shown generally at 10. Device 10 in a false tooth forms hardened cusp means. The device includes plural, substantially spherical elements 12. Elements 12 are B-B like structures, which may be made of stainless steel. Elements 12 are retained in a predetermined pattern by tangential welds 14 which are made between adjacent elements.

Elements 12 may be formed into a four-element array, as shown in FIG. 1, or may be formed into arrays having other numbers of elements.

Figure 2:
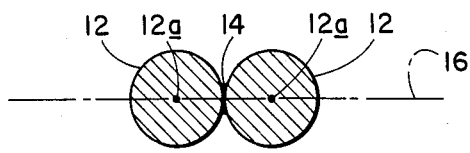
FIG. 2 is a section taken through the array of FIG. 1, generally along the line 2—2.

Turning now to FIG. 2, each element 12 has a center 12a, which, when the elements are formed in an array by welds 14, define a plane, which is represented by the dashed-dot line 16. Welds 14, in the case of a four-element array, as shown in FIG. 1, also lie substantially in plane 16.

Figure 3:
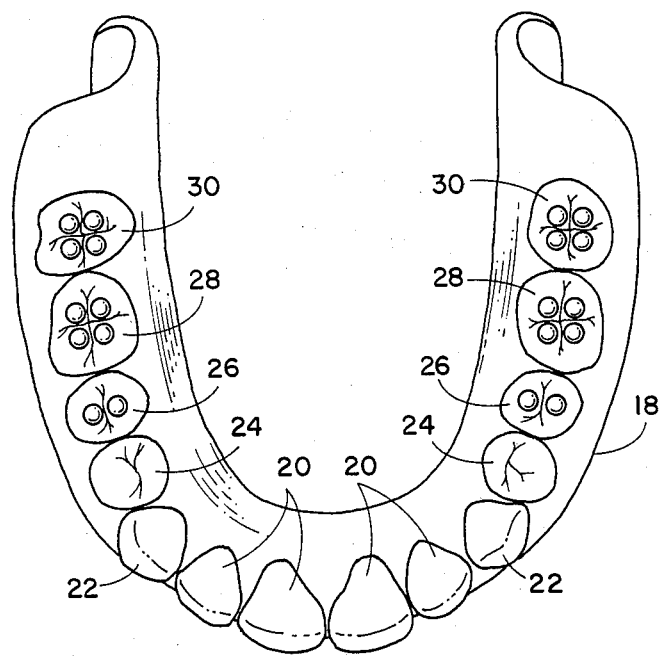
FIG. 3 is a top view of a lower denture incorporating the array of FIG. 1.
Figure 4:
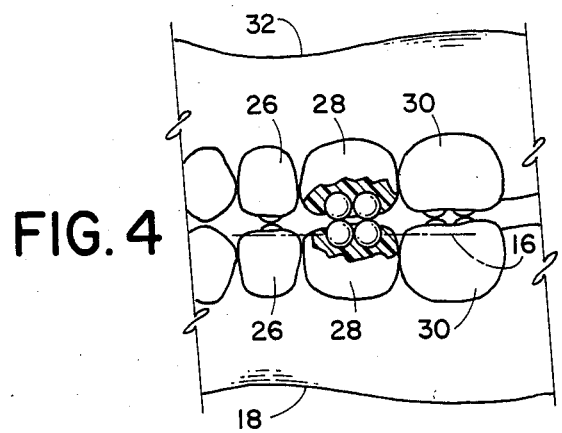
FIG. 4 is a side elevation of a portion of an upper and lower denture incorporating the array of FIG. 1, with portions broken away to show detail.

Turning now to FIGS. 3 and 4, dentures which incorporate device 10 are shown. A lower denture 18 is shown in FIG. 3. Denture 18 includes four incisors 20, canines 22, 1st bicuspids 24, 2nd bicuspids 26, 1st molars 28 and 2nd molars 30.

Device 10 is thought best suited for inclusion in the posterior teeth, which include the second bicuspids and the molars. As shown in FIGS. 3 and 4, a two-element array is embedded in 2nd bicuspids 26, and four element (exemplified by device 10) arrays are embedded in the molars.

Turning now to FIG. 4, lower denture 18 is shown opposite an upper denture 32. The upper and lower dentures are formed from suitable denture material, such as acrylic plastic. While such material provides a natural appearance and provides a generally adequate chewing mechanism, it is not capable, for reasons previously mentioned, of providing as much chewing force as are natural teeth.

A natural tooth has somewhat flattened cusps which meet on a relatively broad surface and which masticate food by a crushing, tearing action. Dentures are not capable of producing the forces required to masticate food in the same manner as are natural teeth, and the provision of natural-like cusps as occlusal surfaces in dentures limits their ability to perform their intended function.

The smaller the surface area point-of-contact between upper and lower teeth, the greater the force which can applied to food. As shown in FIG. 4, point contact is made between elements 12 in the upper and lower dentures. This allows the exertion of the maximum amount of force on the food during the chewing process. Formation of the denture material into a point-contact configuration would be ineffective, as the denture material, although capable of being formed into natural appearing gums and teeth, is of insufficient hardness to withstand the forces created during a point-contact. The material of element 12, stainless steel, has a hardness substantially greater than that of natural teeth or the tooth forming material used in dentures.

Elements 12 in upper denture 32 form what is referred to as upper occlusal surface means. Likewise, elements 12 which embedded in lower denture 18 form a lower occlusal surface means.

The elements are arranged in opposing, offset patterns in the upper and lower teeth, much as are naturally occurring cusps. However, due to the spherical shape of the elements, they are able to provide a point-contact which provides a greatly enhanced chewing surface. The presence of elements 12 in the upper and lower dentures give the appearance of normal amalgam filling and look no more unnatural than do normal fillings which are frequently found in adult teeth.

As is depicted in FIG. 4, an array of elements is placed in a tooth with a major portion of each element 12 in the array embedded in the tooth or denture material. Specifically, plane 16 of the array is located below the natural occlusal surface of the tooth, allowing a portion of element 12 to protrude through the top, occlusal surface of the tooth.

As the wearers' jaws are moved in a normal chewing action, lateral shifting of the dentures relative to one another provides a sliding action between elements 12 and provides for grinding of food. Point contact made between the elements exerts the maximum amount of force obtainable for any given wearer. Because the elements which are doing the contacting are made from stainless steel, there is virtually no wear of the elements, which may remain in service for an extended period of time.

An array is held in place by the material forming the denture or tooth. Tangential welds 14 and the tooth forming material function as means retaining the cusp means in a predetermined pattern.

Although a preferred embodiment of the device of the instant invention has been disclosed herein, it should be appreciated that variations and modifications may be made thereto without departing from the spirit of the invention.

It is claimed and desired to secure by Letters Patent:

1. In combination with upper and lower dentures where the upper denture has an upper multi-cusp posterior tooth body simulating an actual tooth and made of hardened denture-forming material and the lower denture has a lower multi-cusp posterior tooth body simulating a natural tooth mating with the tooth body of the upper denture and made of denture material, the improvement comprising:

an upper occlusal surface element anchored in the posterior tooth body of the upper denture;

a lower occlusal surface element anchored in the posterior tooth body of the lower denture;

the upper and the lower occlusal surface elements each having a composition of greater wear resistance than the denture material and each having hemispherical protrusions limited to paired protrusions that protrude from the tooth body in which the element is anchored, the protrusions of a pair of protrusions being aligned in a direction extending from the buccal to the opposite side of a tooth body; and the protrusions of said upper and lower occlusal surface elements being arranged to simulate naturally occurring cusps in the respective tooth bodies and providing point-contact mastication surfaces.

2. In combination with upper and lower dentures for the human jaw, an artificial tooth in the upper denture and an artificial tooth in the lower denture mating with the tooth in the upper denture and both teeth substituting for posterior multiple cusp natural teeth in the human mouth, each artificial tooth comprising a tooth body having the general configuration of the natural tooth and formed of hardened denture-forming material, and an integral cusp-presenting metallic element anchored in the denture-forming material of the tooth body, said element including hemispherical protrusions limited to paired protrusions that protrude from the tooth body and that are aligned in a direction extending from the buccal to the opposite side of the tooth body and that are located approximately where the cusps of the natural tooth are located, the remainder of the element being embedded in the denture-forming material of the tooth body and rigidly uniting the protrusions, the hemispherical protrusions in the artificial tooth of the upper jaw with the denture in place opposing the protrusions of the artificial tooth in the lower jaw with the denture in place, and the hemispherical protrusions of the two artificial teeth cooperating to provide point contact occlusal surfaces that work against each other.

* * * * *